(12) United States Patent
Lai et al.

(10) Patent No.: US 8,911,672 B2
(45) Date of Patent: Dec. 16, 2014

(54) ELECTRONIC CENSER

(75) Inventors: Chih-Chen Lai, New Taipei (TW);
Han-Lung Lee, New Taipei (TW);
Ga-Lane Chen, Santa Clara, CA (US)

(73) Assignee: Hon Hai Precision Industry Co., Ltd., New Taipei (TW)

( * ) Notice: Subject to any disclaimer, the term of this patent is extended or adjusted under 35 U.S.C. 154(b) by 427 days.

(21) Appl. No.: 13/459,096

(22) Filed: Apr. 28, 2012

(65) Prior Publication Data

US 2013/0115140 A1 May 9, 2013

(30) Foreign Application Priority Data

Nov. 7, 2011 (CN) .......................... 2011 1 0347445

(51) Int. Cl.
*A62B 7/08* (2006.01)
*A61L 9/03* (2006.01)
*A61L 9/00* (2006.01)

(52) U.S. Cl.
CPC ........................................ *A61L 9/03* (2013.01)
USPC ................ 422/125; 422/120; 422/123; 422/5

(58) Field of Classification Search
USPC ....................... 422/120, 123, 125, 5
See application file for complete search history.

(56) References Cited

U.S. PATENT DOCUMENTS

| | | | |
|---|---|---|---|
| 6,635,832 B1 * | 10/2003 | Oster et al. | 200/6 A |
| 2002/0176704 A1 * | 11/2002 | Roe | 392/393 |
| 2006/0023467 A1 * | 2/2006 | Coushaine et al. | 362/555 |
| 2008/0130266 A1 * | 6/2008 | DeWitt et al. | 362/96 |
| 2012/0147624 A1 * | 6/2012 | Li et al. | 362/609 |
| 2014/0168945 A1 * | 6/2014 | Lai | 362/96 |

* cited by examiner

*Primary Examiner* — Regina M Yoo
(74) *Attorney, Agent, or Firm* — Novak Druce Connolly Bove + Quigg LLP

(57) ABSTRACT

An electronic censer includes a censer body, an incense branch and a circuit board. The circuit board is received in the censer body. The incense branch is positioned on the circuit board and includes a heat dissipating board, a light-emitting diode, a first incense core, a second incense core enclosing the first incense core and a reflecting layer on a periphery of the second incense core. A tubular passage is defined between a periphery sidewall of the first incense core and a sidewall of the heat dissipating board to receive liquid fragrance therein. Heat generated by the LED is transferred to the liquid fragrance via the heat dissipating board. Vapor of the liquid fragrance and light of the LED leave the electronic censer via a top of the incense branch.

13 Claims, 3 Drawing Sheets

ELECTRONIC CENSER

BACKGROUND

1. Technical Field

The present disclosure generally relates to a censer, and particularly to an electronic censer.

2. Description of Related Art

Traditional censers are used for accommodating incenses, each of which mainly includes a rod made of bamboo and aromatic biotic materials coated on the rod. When the aromatic biotic materials are burned, they release large amounts of smoke. The burning incenses could ignite other articles to burn which may cause fire; furthermore, the released smoke not only pollutes the environment, but also is harmful to health.

Therefore, what is needed is to provide an electronic censer capable of overcoming the above shortcomings.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure.

DETAILED DESCRIPTION

Reference will now be made to the drawings to describe the present electronic censer, in detail.

Figure 1:
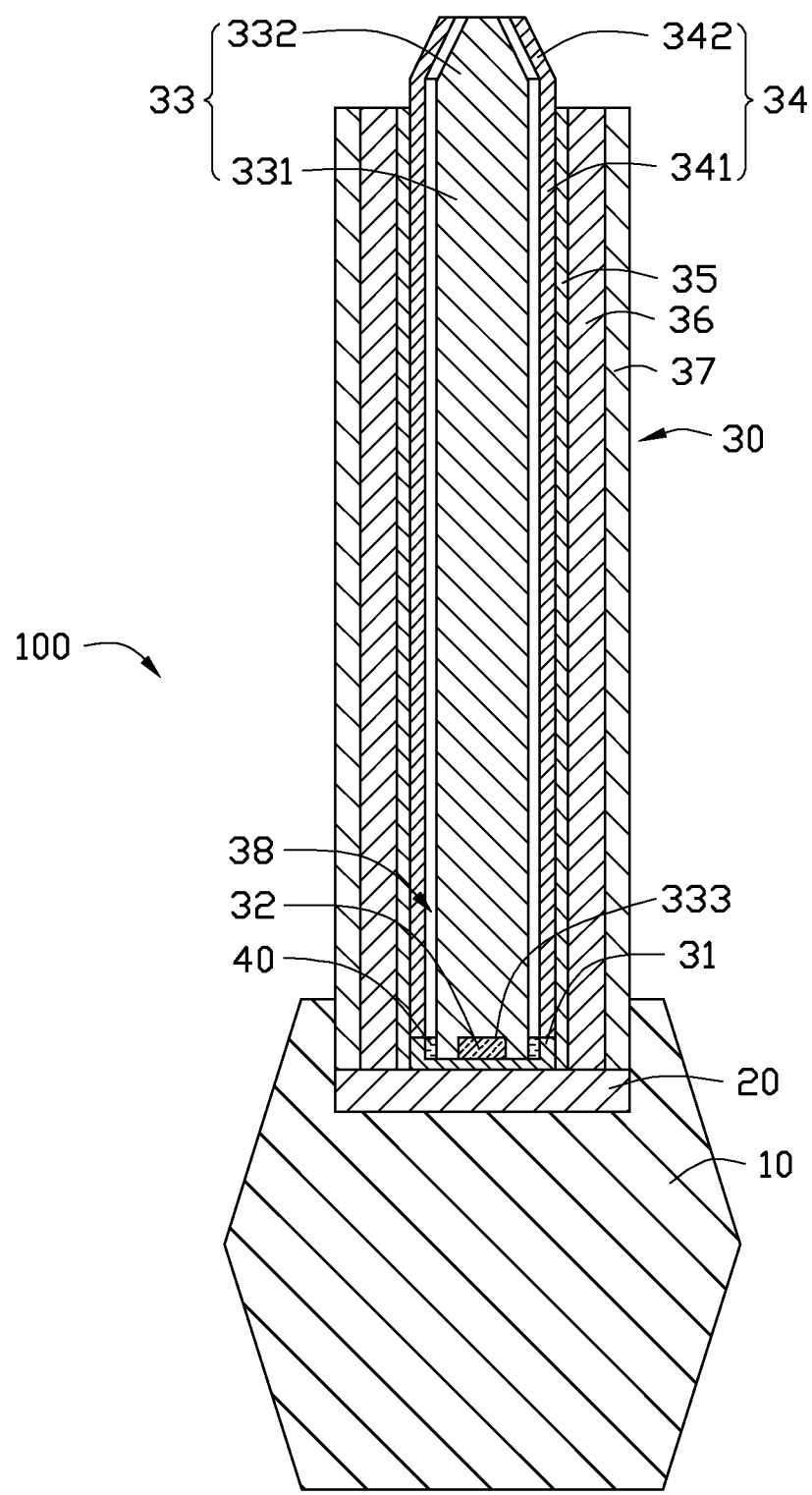
FIG. 1 is a schematic, cross-sectional view of an electronic censer according to one embodiment of the present disclosure.

Referring to FIG. 1, an electronic censer 100 according to an exemplary embodiment of present disclosure is shown. The electronic censer 100 includes a censer body 10, a circuit board 20 received in the censer body 10, and an incense branch 30 positioned on the circuit board 20 and extending upwardly from the censer body 10.

The censer body 10 is a hollow container with an opening at a top thereof. The censer body 10 is used for receiving the circuit board 20 and a bottom part of the incense branch 30. The censer body 10 can have various shapes. A removable lid (not shown) can be provided for sealing the opening of the censer body 10 when the incense branch 30 is removed to prevent dust from entering the censer body 10.

The circuit board 20 is received in the censer body 10. The circuit board 20 is for holding the incense branch 30 thereon and providing electrical power to it. There are only one circuit board 20 and one incense branch 30 shown in the embodiment. Alternatively, the electronic censer 100 can be equipped with multiple circuit boards 20 holding multiple incense branches 30.

The incense branch 30 includes a heat dissipating board 31, a light-emitting diode (LED) 32 positioned on the heat dissipating board 31, a first incense core 33 covering the LED 32, a second incense core 34 enclosing the first incense core 33, a reflecting layer 35 configured on an outer periphery of the second incense core 34, a shading layer 36 configured on an outer periphery of the reflecting layer 35, and a baking paint layer 37 configured on an outer periphery of the shading layer 36.

Figure 2:
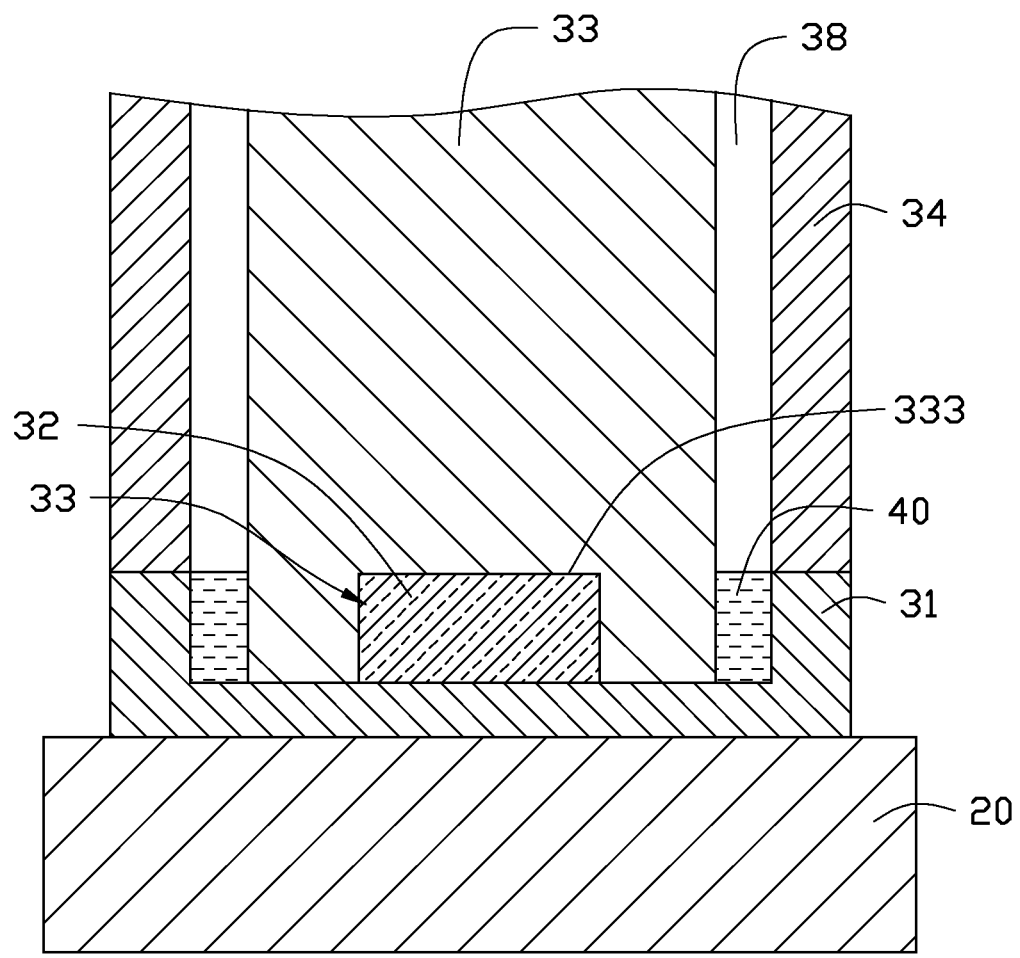
FIG. 2 is a partially enlarged view of the electronic censer of FIG. 1.
Figure 3:
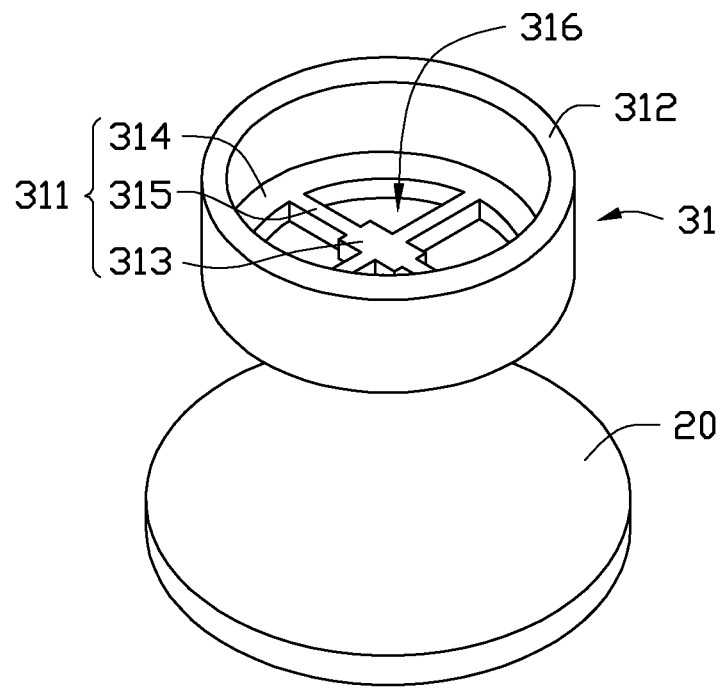
FIG. 3 is an exploded, schematic view of a circuit board and a heat dissipating board of an incense branch of the electronic censer of FIG. 1.

Referring to FIG. 2 and FIG. 3, the heat dissipating board 31 includes a main body 311 and an annular sidewall 312 surrounding the main body 311. In this embodiment, the sidewall 312 is integrally formed with the main body 311 as a single piece, and extends upwardly from an outer periphery of the main body 311.

The main body 311 includes a base 313, an engaging portion 314, and a plurality of ribs 315 interconnecting the base 313 and the engaging portion 314. The base 313 has a rectangle shape for holding the LED 32 thereon and absorbing heat generated by the LED 32. The engaging portion 314 is annular, and engages with the annular sidewall 312. The base 313, the ribs 315, and the engaging portion 314 cooperatively define a plurality of hollow structures 316 therebetween. In this embodiment, there are four ribs 315, and the four ribs 315 and the base 313 cooperatively form a cross.

The sidewall 312 extends upwardly and vertically from an outer periphery of the engaging portion 314. The sidewall 312 receives a bottom end of the first incense core 33 therein, and a top of the sidewall 312 engages with a bottom of the second incense core 34. The sidewall 312 absorbs heat generated by the LED 32 from the main body 311.

The first incense core 33 is made of light transmissive material, and includes a first light guiding portion 331 and a first light output portion 332 at a top end of the first light guiding portion 331. In this embodiment, the first incense core 33 is made by injection molding of plastic. The first light guiding portion 331 defines a groove 333 in a bottom thereof for receiving the LED 32 therein. An outer diameter of the first light guiding portion 331 is smaller than an outer diameter of the engaging portion 314 but larger than an inner diameter of the engaging portion 314. The first light output portion 332 is shaped to be a cone with a sandblasted outer surface, so that light will be output through the outer surface of the light output portion 332 uniformly.

The second incense core 34 is hollow and cylindrical, and also made of light transmissive material. The second incense core 34 extends upwardly from the top of the sidewall 312. The second incense core 34 includes a second light guiding portion 341 and a second light output portion 342 at a top end of the second light guiding portion 341. In this embodiment, the second incense core 34 is also made by injection molding of plastic. The second light guiding portion 341 is parallel to the first light guiding portion 331, and has a thickness substantially equal to that of the sidewall 312. The second incense core 34 and the first incense core 33 cooperatively form an annular gap 38 therebetween which functions as a fluid passage for injecting liquid fragrance 40 into the electronic censer 100 and flowing of vaporized fragrance out of electronic censer 100. The second light output portion 342 is shaped to be a hollow cone with an uneven outer surface, so that the light will be uniformly output therefrom. The second light output portion 342 tapers gradually along a direction away from the second light guiding portion 341. The second incense core 34, the first incense core 33, and the sidewall 312 and the engaging portion 314 of the heat dissipating board 31 cooperatively define a bottom of the annular gap 38 therebetween. Alternatively, the sidewall 312 is omitted, and the second light guiding portion 341 of the second incense core 34 extends downwardly to the engaging portion 314 of the heat dissipating board 31. In other words, the bottom of the gap 38 is defined among the second light guiding portion 341 of the second incense core 34, the engaging portion 314 of the heat dissipating board 31, and the first light guiding portion 331 of the first incense core 33.

The liquid fragrance 40 is constantly provided in the bottom of the gap 38. The liquid fragrance 40 can be vaporized into white vapor under proper temperature. The white vapor has an odor like that generated by smoke of a burning conventional incense. The vapor leaves the incense branch 30 through a top of the gap 38 thereby to produce an effectiveness of a burning incense. In this embodiment, the liquid fragrance 40 is received in the bottom of the gap 38 between the sidewall 312 and the first incense core 33, and the vaporization temperature of the liquid fragrance 40 is about 60 degrees centigrade.

The LED 32 is located on the base 313 of the heat dissipating board 31, and received in the groove 333 of the first light guiding portion 331 of the first incense core 33. The LED 32 is electrically connected to the circuit board 20, and isolated from the liquid fragrance 40 by the first incense core 33. During operation, the light emitted from the LED 32 passes through the first and second light guiding portions 331, 341, and towards a top of the incense branch 30, then outputs from the first and second light output portions 332, 342.

The reflecting layer 35 can be a reflective film for reflecting light. As such, the light emitted by the LED 32 will be totally reflected back into the incense branch 30, which prevents light from scattering out via a sidewall of the incense branch 30.

The shading layer 36 is coated on the outer periphery of the reflecting layer 35. The shading layer 36 is made of black paint, while, the shading layer 36 can also be made by a film with other colors. The shading layer 36 can further prevent light from scattering out via the sidewall of the incense branch 30.

The baking paint layer 37 can be made by spraying mulberry plastic paint onto the outer periphery of the shading layer 36 and then baking the paint. Thus, the incense branch 30 can have an appearance like that of a conventional incense. The first and second light output portions 332, 342 are located above the reflecting layer 35, the shading layer 36 and the baking paint layer 37.

In the electronic censer 100, the circuit board 20 drives the LED 32 to emit light. Both the first incense core 33 and the second incense core 34 transmit lights to the top end of the incense branch 30. The first incense core 33, the second incense core 34 and the heat dissipating board 31 cooperatively define the gap 38 therebetween to receive the liquid fragrance 40. The heat dissipating board 31 uses the heat of the LED 32 to heat the liquid fragrance 40 into vapor, which leaves the incense branch 30 from the top end of the incense branch 30. As such, the electronic censer 100 can simulate the burning effectiveness of a conventional censer, while the electronic censer 100 is more safe, environmental friendly and unharmful to the health of the user, since it is more easily to control the quality/composition of the liquid fragrance 40 of the disclosure than the aromatic biotic powder used in manufacturing the conventional incense.

It is to be understood that the above-described embodiments are intended to illustrate rather than limit the disclosure. Variations may be made to the embodiments without departing from the spirit of the disclosure as claimed. The above-described embodiments illustrate the scope of the disclosure but do not restrict the scope of the disclosure.

What is claimed is:

1. An electronic censer comprising:
    a censer body, which is a hollow container with an opening at a top thereof;
    a circuit board received in the censer body;
    an incense branch positioned on the circuit board and extending upwardly from the censer body, the incense branch comprising an LED electrically connected to the circuit board, a first incense core made of light transmissive material, a second incense core, a gap being defined between the first and second incense cores, and a heat dissipating board positioned on the circuit board, the second incense core being hollow cylindrical and enclosing the first incense core, the first incense core, the second incense core and the heat dissipating board cooperatively defining a bottom of the gap therebetween adapted to receive liquid fragrance therein, the LED being received in a bottom of the first incense core adjacent to the heat dissipating board, and isolated from the liquid fragrance, wherein when the LED is operated to emitting light, the light radiates out of the incense branch through tops of the first and second incense cores, and heat generated by the LED heats the liquid fragrance to generate vapor which leaves the incense branch from a top of the gap.

2. The electronic censer according to claim 1, wherein the first incense core is located on the heat dissipating board, the first incense core defining a groove in the bottom thereof adjacent to the heat dissipating board, the LED being received in the groove and isolated from the liquid fragrance by the first incense core.

3. The electronic censer according to claim 2, wherein the first incense core comprises a first light guiding portion and a first light output portion at a top of the first light guiding portion away from the heat dissipating board, the groove being defined in a bottom of the first light guiding portion, the first light output portion being shaped to be a cone, the first light output portion tapering along a direction away from the first light guiding portion.

4. The electronic censer according to claim 1, wherein the heat dissipating board comprises a main body and a sidewall surrounding the main body, the sidewall extending upwardly from an outer periphery of the main body, the first incense core being disposed on the main body, the second incense core being disposed on a top of the sidewall, the liquid fragrance being in thermally connection to the heat dissipating board.

5. The electronic censer according to claim 4, wherein the main body comprises a base, an engaging portion, and a plurality of ribs interconnecting the base and the engaging portion, the engaging portion engaging with the sidewall, the LED being positioned on the base.

6. The electronic censer according to claim 5, wherein the second incense core is located on the sidewall, an outer diameter of the first light guiding portion being smaller than an outer diameter of the engaging portion but larger than an inner diameter of the engaging portion, the gap being cooperatively defined among the second incense core, the first incense core, and the sidewall and the engaging portion of the heat dissipating board.

7. The electronic censer according to claim 4, wherein the second incense core is made of light transmissive material, and comprises a second light guiding portion in connection with the heat dissipating board, a thickness of the second light guiding portion being substantially equal to that of the sidewall.

8. The electronic censer according to claim 7, wherein the second incense core further comprises a second light output portion located at a top of the second light guiding portion away from the heat dissipating board, the second light output portion being shaped to be a hollow cone with an uneven outer surface, the second light output portion tapering along a direction away from the second light guiding portion.

9. The electronic censer according to claim 1, wherein the incense branch further comprises a reflecting layer on an outer periphery of the second incense core.

10. The electronic censer according to claim 9, wherein the incense branch further comprises a shading layer, the shading layer being configured on an outer periphery of the reflecting layer.

11. The electronic censer according to claim 10, wherein the incense branch further comprising a baking paint layer, the baking paint layer being configured on an outer periphery of the shading layer and having a color of a mulberry.

12. The electronic censer according to claim 10, wherein the shading layer is black.

13. The electronic censer according to claim 10, wherein the first and second incense cores each have a top above a top of each of the baking paint layer, the shading layer and the reflecting layer.

* * * * *